United States Patent [19]
Johnson et al.

[11] 4,204,322
[45] May 27, 1980

[54] DENTURE HOLD APPARATUS

[76] Inventors: John N. Johnson, P.O. Box 614, Orange, Tex. 77630; Charles J. Lindenberger, 508 S. Gardenia Dr., Melbourne, Fla. 32901

[21] Appl. No.: 882,989

[22] Filed: Mar. 3, 1978

[51] Int. Cl.² .............................................. A61C 13/24
[52] U.S. Cl. .................................................. 433/185
[58] Field of Search ........................................... 32/3, 8

[56] References Cited

U.S. PATENT DOCUMENTS

| | | |
|---|---|---|
| 1,184,187 | 5/1916 | Linares ..................................... 32/3 |
| 2,165,558 | 7/1939 | Linchitz .................................... 32/3 |
| 2,510,184 | 6/1950 | Lynn ......................................... 32/3 |
| 2,897,594 | 8/1959 | Kopec et al. ............................. 32/3 |
| 3,409,985 | 11/1968 | Graceffo ................................... 32/3 |
| 3,555,683 | 1/1971 | Gregorovic ............................... 32/3 |
| 3,644,997 | 2/1972 | Fernandez ................................. 32/3 |
| 3,722,096 | 3/1973 | Kopfer et al. ............................. 32/3 |
| 3,750,287 | 8/1973 | Bloom ....................................... 32/3 |
| 3,787,974 | 1/1974 | Gaylord .................................... 32/3 |

FOREIGN PATENT DOCUMENTS

1090820 10/1960 Fed. Rep. of Germany ................ 32/3

Primary Examiner—Russell R. Kinsey
Assistant Examiner—Michael J. Foycik, Jr.
Attorney, Agent, or Firm—Gunn and Lee

[57] ABSTRACT

Apparatus for securing a denture plate in position is disclosed. The illustrated and preferred embodiment incorporates a vacuum pump which has the exterior form and shape of a tooth embedded in a denture plate. The tooth incorporates a reciprocally operated pump. The pump pulls air from an exposed, lower indention or chamber. This chamber is connected via multiple passages to similar chambers around the denture, all of the chambers collectively open to the gum of the wearer. As air is evacuated from the chambers, a vacuum is formed. The vacuum increases holding power of the denture against the gum.

9 Claims, 2 Drawing Figures

DENTURE HOLD APPARATUS

BACKGROUND OF THE PROBLEM

Many people must wear dentures. A particular problem arises in holding a lower denture on the gum. This problem is much more common in the lower denture than in the upper denture. In the lower denture, it does not have comparable surface area in contact with the gum compared to the upper denture. The reduced surface area thus decreases the holding surface. So to speak, it is merely perched on the gum, somewhat precariously, and is able too easily to flop upwardly and downwardly. When the user eats various and sundry foods which are difficult to chew, the lower denture will become unstable. The instability takes the form of denture flopping. As it rises from the gum as the user opens his mouth further during chewing, it becomes slightly free. A small gap is formed under the denture. The gap formation is accompanied by suction under the denture. The suction, however light, draws partly chewed food under the denture. This would not be too great a problem if the partly chewed food were soft and pliant. However, it is just as likely to be crumbs of food which are rather crunchy, thereby giving the user discomfort. This discomfort is quite severe in some instances. The severity, of course, relates to the vigor of the user in chewing and other factors.

Various and sundry devices have been attempted for the purpose of reducing denture slippage. They operate by differing theories. It is submitted that the present disclosure is directed to a very functional device. It is particularly successful in that it does not provide extreme gripping force when the user is not chewing vigorously. This, of course, occurs at a time when a good grip is not important. By contrast, vigorous chewing is accompanied by increased gripping by the present invention. The grip is increased by the first few flexures of the user's jaw. A quick increase in the grippage goes a long way in holding the denture in place. Prolonged chewing beyond that sustains and somewhat increases the gripping force.

BRIEF DESCRIPTION OF THE DISCLOSED EMBODIMENT

The present disclosure is directed to a lower denture gripping mechanism. In the denture itself, one tooth is constructed with a flexible plastic shell or housing. It encloses a pump mechanism. The pump mechanism draws air from a chamber on the nether side. The pump mechanism operates two valves, one functioning as an inlet check valve and the other being an outlet exhaust valve. The chamber itself is exposed to the gum of the user. The grip on the jaw or gum is increased by pulling a vacuum in the chamber, the chamber being located in the denture itself.

The device includes multiple chambers around the denture, and they are all connected together through common lateral passages. This provides balanced grip at various points around the denture. The grip is successful because the denture fits snugly against the gum of the user and has a flange-like construction protruding adjacent to and around the chambers so that leakage is minimized.

DETAILED DESCRIPTION OF THE ILLUSTRATED EMBODIMENT

Figure 1:
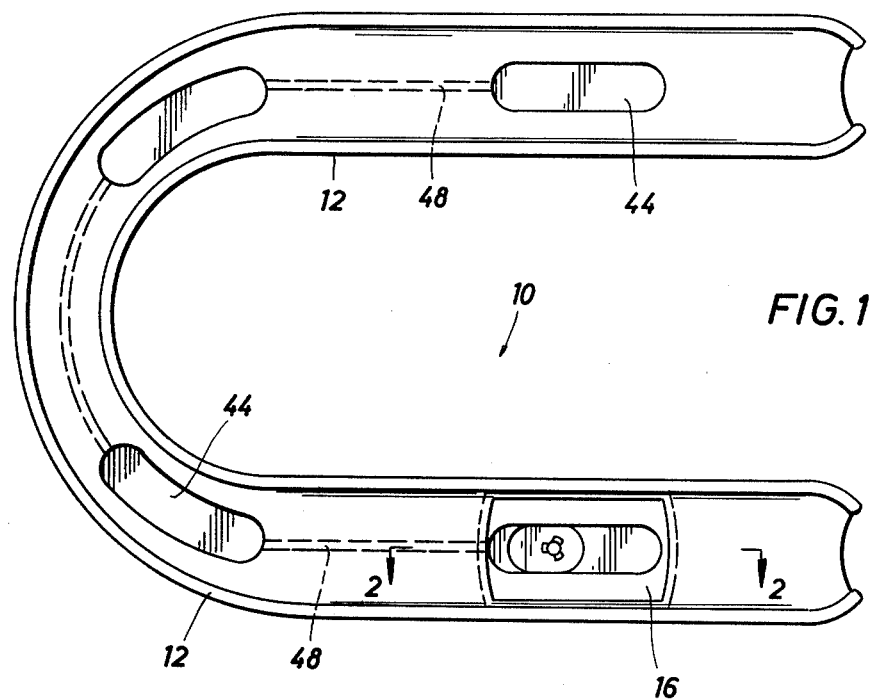
FIG. 1 discloses a lower denture plate modified in accordance with the teachings of the present disclosure.

Attention is first directed to FIG. 1 of the drawings where the numeral 10 identifies the denture plate of the present invention. In many regards, the denture plate is well known in that it includes a simulated set of teeth. It is generally U-shaped as viewed from the top. It is presumed that it is a full, not a partial plate. The full plate thus is U-shaped to rest on the entire gum of the user. It typically is constructed with simulated teeth, and a typical number is about sixteen simulated teeth. The denture plate 10 of the present invention is, on the exterior, similar to any other denture plate in that it has an overhanging flange 12 which nests against the gum, and it also includes conventional simulated teeth at all locations except one. The one location which is different has the external appearance of a simulated tooth, but it is constructed and arranged with a pump in the tooth as will be described.

The modified tooth incorporating a pump is identified by the numeral 14. The tooth, itself, is immediately adjacent to a gripping chamber 16. The chamber 16 is closed over on all sides except the bottom face. It is defined in the flange 12 which surrounds it at the edges. Moreover, the open face of the chamber 16 is adapted to be closed over by the gum of the user. As will be understood, the flange normally maintains smooth and broad contact against the gum of the user. The quality of the contact depends on a number of factors, including the smoothness of the flange, the trueness of the flange shape to the gum shape of the user, the regularity of the surface of the user, and many other factors. More importantly, there may be some leakage into the chamber under the flange. Such leakage will normally draw saliva into it, and this serves as a sealing fluid. The surface tension of the saliva helps hold the denture against the gum, at least providing a light gripping force. It also provides a means of resisting air flow under the flange. The importance of this will be understood hereafter.

It will be observed that the modified tooth 14 is not symmetrically centered in the denture 10. It is located to simulate a molar tooth, not an incisor tooth. The simulated molar tooth is larger to enable the equipment to be described to be incorporated within it.

Figure 2:
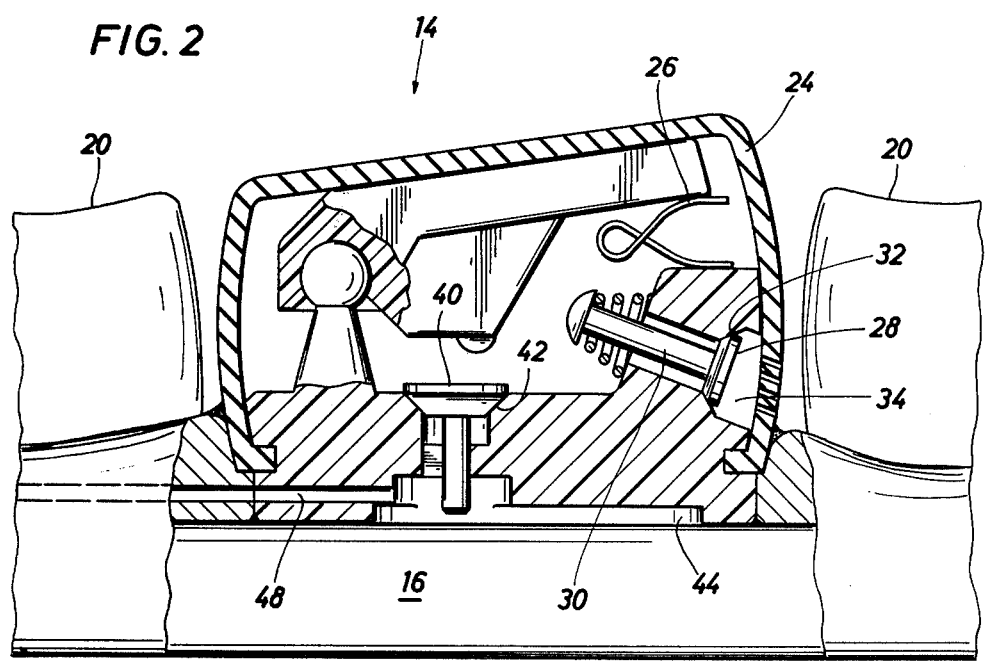
FIG. 2 is an enlarged detailed view of an air pump in the denture plate of FIG. 1.

Attention is next directed to FIG. 2 of the drawings. There, the simulated tooth 14 is shown in greater detail. The numeral 20 identifies the crown or the top edge of adjacent teeth. They stand above the denture flange plate 12 by a specified distance, as constructed by the dentist. They cannot be too tall or too short. If too tall, the user cannot close his jaws comfortably and will get inadequate chewing action. If too short, discomfort of another sort will occur. The crown line preferably remains true to that which existed prior to fitting of the denture. This simulated shape remains true to the shape of the mouth of the user before losing his permanent teeth.

The modified tooth 14 includes an outer plastic shell 24. The plastic shell or housing has the external appearance and shape of a molar tooth. The external appearance or shape conforms to the neighboring molar teeth in all regards, except that the modified tooth 14 is somewhat taller. It is taller to enable a pumping action to occur. The operating equipment is within the plastic shell 24.

The plastic shell is formed of a flexible plastic. It preferably has a relatively thick wall. Such thickness enables it to flex and bend without puncturing or becoming brittle. This, of course, also depends in large part on the choice of the material and the thickness of which it is constructed. The plastic shell or cover is completely embedded around its periphery. It is somewhat in the form of an inverted container. It is hollow on the interior. As shown in the drawings, it is anchored or rooted to the denture 10 to define an internal pump chamber which, but for the passages to be described, would be a closed chamber. The plastic shell thus encloses equipment to be described. The plastic shell can have an external appearance which is coated, or a color pigment is impregnated into the plastic. It preferably has the appearance and general profile of a molar tooth. The appearance is primarily for uniformity to achieve a desired cosmetic appearance. Of course, the tooth 14 is fairly well recessed in the mouth of the user and cannot be readily viewed in ordinary circumstances by anyone else.

It will be appreciated and understood that the flange 12 thickens from its outer edge. At its outer edge, it is relatively thin. As it thickens at the middle, it incorporates substantial strength and body for structural integrity of the denture plate 10. In the central portion where the molar teeth are located, particularly in a ridge line along the denture, the plastic shell 24 is anchored and rooted into the rigid flanged body. Here, the plastic shell is anchored, as by example, by the application of an epoxy resin glue.

The plastic shell 24 thus encloses the operative equipment. The equipment on the interior is quite small. It is, nevertheless, adequate for purposes to be described. The resiliency of the plastic material restores the plastic shell to its noncompressed state. This can be assisted by a resilient means 26. The plastic shell could fatigue after a period of time and no longer stand erect.

It is helpful that the tooth 14 stands somewhat above the adjacent teeth. This enables it to be pushed by the teeth on the upper jaw. Such a push is very valuable in that the push is a compressive stroke applied to the pumping tooth 14.

The resilient means 26 is a restoring mechanism to restore the plastic shell in its original shape. The shell is constructed and arranged so that it develops its own upwardly directed restoring force to the plastic shell. The restoring force comes into play as the user separates his jaws during chewing, thereby enabling the pumping tooth to be restored to its full, erect condition. The plastic shell is depressed when chewing occurs by contact of the upper teeth against the lower teeth.

Additional equipment is included inside the plastic shell 24. The numeral 28 identifies an outlet exhaust valve. The valve 28 is mounted on a valve stem 30 for ease of movement. There is a valve seat 32. The valve seat seals against the valve when it is closed. When it is open, the valve seat opens into a valve passage 34 which exhausts air from the interior of the plastic shell. The outlet passage opens to the exterior. The outlet passage is a path whereby air inside the tooth is expelled.

Assume for the moment that the plastic shell 24 is depressed by about fifty percent of its height. In this event, the pressure on the interior may very well double. As it doubles, air is forced out of the outlet passage 34 on flowing past the valve 28. The flow is past the valve seat 32. When pressure in the tooth is approximately equal to the external pressure, the valve 28 closes against the valve seat 32. Thus, air is exhausted through the passage 34, but no air is drawn in through this passage.

The numeral 40 identifies an inlet valve. The inlet valve 40 communicates from the gripping chamber 16 into the plastic shell 24. The valve 40 is a reverse flow check valve. It permits flow out of the chamber 16 into the tooth. It forbids flow in the opposite direction. The valve 40 cooperates with a valve seat 42. In addition, it relies on its shape, its position for gravity pull and small clearance to restore it to the closed position. As desired, a return spring can be used.

Inlet valve 40 has a cycle of operation which is out of synchronization with the other valve. When the valve 28 is open, the valve 40 is closed. When the valve 40 is open, the valve 28 is normally closed. The valve 40 opens to introduce air into the plastic shell 24. The valve 28 opens only during expulsion of air. Thus, air flows with each cycle of operation from the chamber 16. As this flow accumulates, air in the chamber 16 is reduced, creating a vacuum which holds the denture more firmly against the gum of the user.

The chamber 16 is located near one end of the U-shaped denture. To obtain a balanced force so that the denture does not wobble, a similar chamber 44 is located under the flange 12 at another location across the mouth of the user. The two are connected together by a passage 48. The passage 48 draws air from the second chamber to the first where it is exhausted by the pumping tooth 14. It will be understood that the pressure in all the chambers is thus reduced, creating a distributed vacuum which applies a more evenly distributed holding force to the denture plate 10. Indeed, more than two chambers can be used. Multiple chambers at various locations around the periphery are quite permissible. It is desirable that the number be kept relatively low and evenly balanced along a centerline through the denture. The relative or aggregate volume of the several chambers is a drag on vacuum creation. In other words, if the several chambers cumulatively hold a substantial volume of air, it will take the pump longer to remove air to achieve a specified vacuum level.

The present invention is particularly advantageous in that it repetitively draws air from the chamber. Suppose the user is a guest at a fairly lengthy formal meal. The meal may, therefore, require at least an hour or so. In such an instance, the denture 10 of the present invention will operate to grip the jaw of the user firmly as it is used. In other words, as the denture experiences chewing, its grip is increased. Should the chewing stop for five or ten minutes, the grip will relax as the air pressure in the chamber 16 restores to atmospheric. Such restoration is achieved through leakage beneath the flange 12.

As the lengthy meal stops and starts again insofar as the use of the denture plate is concerned, renewed pumping on the pumping tooth 14 renews the vacuum. The first few strokes after a long period of inactivity make quite a change in pressure within the chamber 16. The next several strokes of the pump do not have quite the marked impact, but they do sustain a high vacuum level. The precise measure of vacuum depends on so many factors that it cannot be specified. One of the most important factors is the rate of leakage under the flange 12 into the chamber 16. The pumping tooth must normally overcome this leakage. It normally can overcome the leakage as long as it is operating. The vacuum holding duration, however, is dependent on the rate of leakage.

Saliva of the user is no particular problem to the present invention. If need be, the plate can be submerged in water and operated by hand to flush water through the plastic shell 24 to clean out the inner workings. Saliva of the user normally serves as a sealant. As a sealant, it prevents or decreases vacuum leakage.

The materials chosen for the present invention should be considered. The flange 12 and the body of the denture plate 10 are constructed of conventional or ordinary denture materials. The plastic shell 24 is preferably formed of a high quality plastic able to undergo millions of flexures without fatigue. The internal working parts can be formed of plastic, also. This is particularly true of the valve components. A high quality metal, such as stainless steel, can be used, also. If desired, the pumping tooth can have a length equal to more than one tooth. The teeth on the denture are typically so close together that it is appropriate to think of several adjacent teeth as being formed of one piece of material when the teeth in the denture are shaped to the desired crown height and mating contours.

The foregoing is directed to the preferred embodiment, but the scope is determined by the claims which follow.

We claim:

1. A pneumatic holding apparatus for use in a denture which comprises a pneumatic tooth pump installed in the denture plate which pneumatic tooth pump is operated by repeated chewing action and wherein said pneumatic tooth pump includes a plastic shell which is sealed into the denture to define an internal closed chamber, an outlet valve from said chamber opening to the exterior to define a path for exhausting air from the closed chamber through said valve, an inlet valve into said chamber, said inlet valve repeatedly permitting air to be drawn into said chamber from an indention formed by a peripherally surrounding flange which flange contacts the gum thereby enclosing said indentation so that air pulled from the indention adjacent the gum of the user forms a partial vacuum holding the denture plate more firmly to the gum of the user as the user chews and the chewing motion repeatedly collapses said plastic shell to repeatedly expel air through the outlet valve.

2. The apparatus of claim 1 wherein said plastic shell sealed against air leakage to define said internal chamber incorporates an internal resilient means for restoring it to a height extending above other teeth in the denture and for restoring that shape after chewing.

3. The apparatus of claim 1 wherein said outlet valve includes a valve, a cooperative valve seat and an outlet passage to the exterior from said chamber.

4. The apparatus of claim 3 including means for guiding said valve toward the valve seat for seating thereagainst to seal said chamber.

5. The apparatus of claim 4 including means for limiting the range of movement of said valve relative to said valve seat.

6. The apparatus of claim 5 wherein said valve passage means includes multiple small ports which in the aggregate form said passage means.

7. The apparatus of claim 2 wherein said plastic shell is supported by a pad mounted in cantilever fashion on a ball and socket joint which is restored to a height extending above other teeth in the denture by said internal resilient means.

8. The apparatus of claim 2 wherein said inlet valve includes a valve and cooperative valve seat and an inlet from the gripping chamber to the inside of said internal closed chamber.

9. The apparatus of claim 2 wherein said resilient means is comprised of the flexure of said plastic shell.

* * * * *